US008551065B2

(12) United States Patent
De Angelis

(10) Patent No.: US 8,551,065 B2
(45) Date of Patent: Oct. 8, 2013

(54) CLOSURE ELEMENT WITH ELASTIC SIDE PANELS FOR ABSORBENT SANITARY PRODUCTS, ABSORBENT SANITARY PRODUCT AND RESPECTIVE MANUFACTURING METHOD

(75) Inventor: Tonino De Angelis, Pescara (IT)

(73) Assignee: Fameccanica.Data S.p.A., Sambuceto di San Giovanni Teatino (Chieti) (IT)

( * ) Notice: Subject to any disclaimer, the term of this patent is extended or adjusted under 35 U.S.C. 154(b) by 299 days.

(21) Appl. No.: 12/518,949

(22) PCT Filed: Mar. 7, 2008

(86) PCT No.: PCT/IB2008/000639
§ 371 (c)(1),
(2), (4) Date: Jun. 12, 2009

(87) PCT Pub. No.: WO2009/019545
PCT Pub. Date: Feb. 12, 2009

(65) Prior Publication Data
US 2010/0022982 A1    Jan. 28, 2010

(30) Foreign Application Priority Data
Aug. 8, 2007   (EP) .................................... 07425518

(51) Int. Cl.
*A61F 13/15*   (2006.01)
*A61F 13/20*   (2006.01)

(52) U.S. Cl.
USPC .......................................... 604/391; 604/387

(58) Field of Classification Search
USPC ..................... 604/386–392, 385.03
See application file for complete search history.

(56) References Cited

U.S. PATENT DOCUMENTS

| 4,014,339 A | 3/1977 | Tritsch |
| 4,237,890 A | 12/1980 | Laplanche |

(Continued)

FOREIGN PATENT DOCUMENTS

| EP | 1 459 721 | 9/2004 |
| EP | 1 523 968 | 4/2005 |

(Continued)

OTHER PUBLICATIONS

International Search Report for PCT/IB2008/000639 mailed Jul. 11, 2008.

(Continued)

*Primary Examiner* — Michele M Kidwell
(74) *Attorney, Agent, or Firm* — Nixon & Vanderhye P.C.

(57) ABSTRACT

A closure element (10) with elastic side panels for absorbent pant-like sanitary products (52), said element (10) being formed starting from a strip (12) at least partially made of elasticised material (16) folded in transverse direction so as to form two parts (22, 24), symmetrical relative to a central transverse plane (26), each of said parts (22, 24) being able to form a side panel (76) of an absorbent sanitary product (52), said closure element (10) comprising: —a first branch (28) that extends continuously through said central transverse plane (26); —two second branches (30) connected to respective opposite ends of the first branch (28) by means of respective first folds (32), distal relative to said central transverse plane (26), in which the first branch (28) and the two second branches (30) have respective mutually facing surfaces (34, 36) permanently fastened to each other; —two third branches (40) connected to respective ends of second branches (30) by means of respective second folds (42), proximal and distanced relative to said central transverse plane (26); —two fourth branches (44) connected to respective ends of the two third branches (40) in distal positions relative to said central transverse plane (26); and—two fifth branches (46) connected to respective ends of the fourth branches (44) by means of respective third folds (48), proximal and distanced relative to said central transverse plane (26).

12 Claims, 7 Drawing Sheets

(56) References Cited

U.S. PATENT DOCUMENTS

Figure 1:
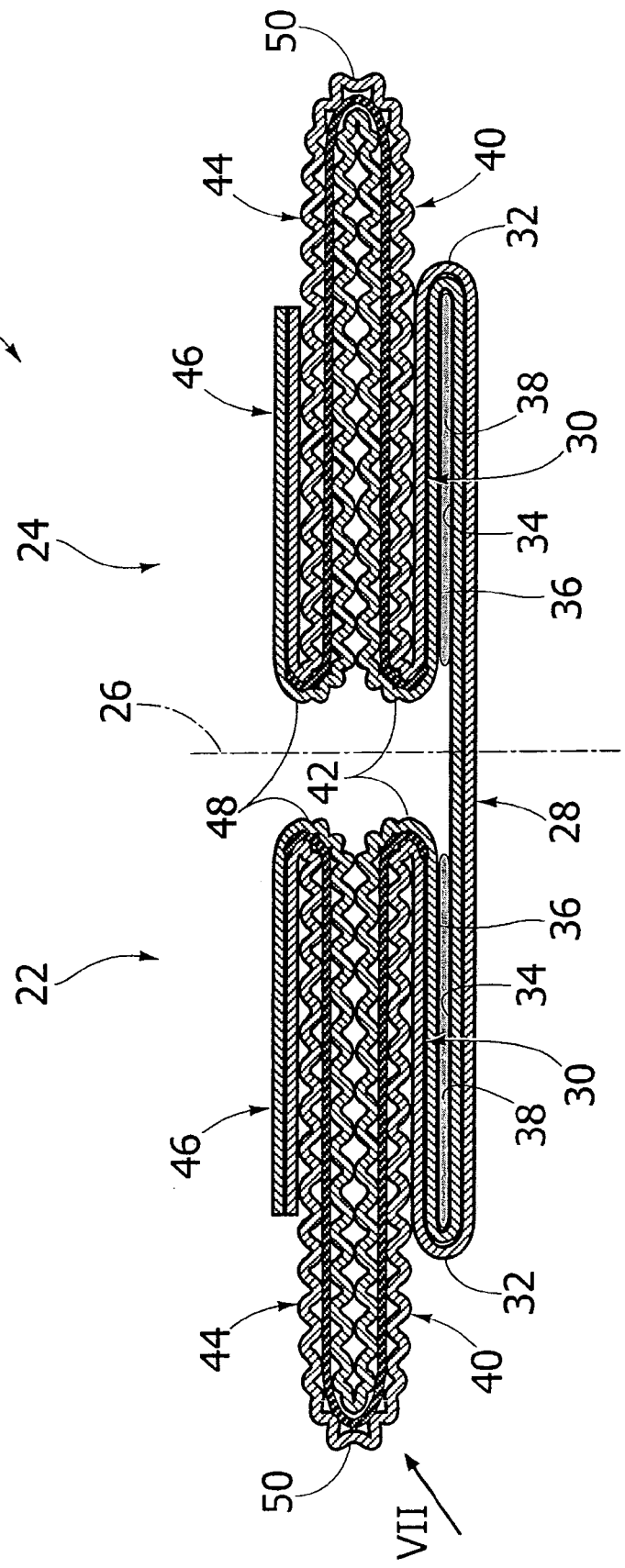

| | | |
|---|---|---|
| 2001/0034512 A1 | 10/2001 | Karlsson et al. |
| 2002/0111596 A1 | 8/2002 | Fletcher et al. |
| 2005/0113793 A1* | 5/2005 | Bianco .......................... 604/391 |
| 2006/0042746 A1 | 3/2006 | Ukegawa |
| 2010/0016823 A1* | 1/2010 | Gabriele ....................... 604/389 |

FOREIGN PATENT DOCUMENTS

| | | |
|---|---|---|
| EP | 1 792 594 A1 | 6/2007 |
| JP | 2006-95277 | 4/2006 |
| JP | 2006-175007 | 7/2006 |
| WO | WO 01/87216 | 11/2001 |

OTHER PUBLICATIONS

Written Opinion for PCT/IB2008/000639 mailed Jul. 11, 2008.
Japanese Patent Office Action dated May 8, 2012, in connection with Japanese Patent Application No. 2010-519532 (English Summary).

* cited by examiner

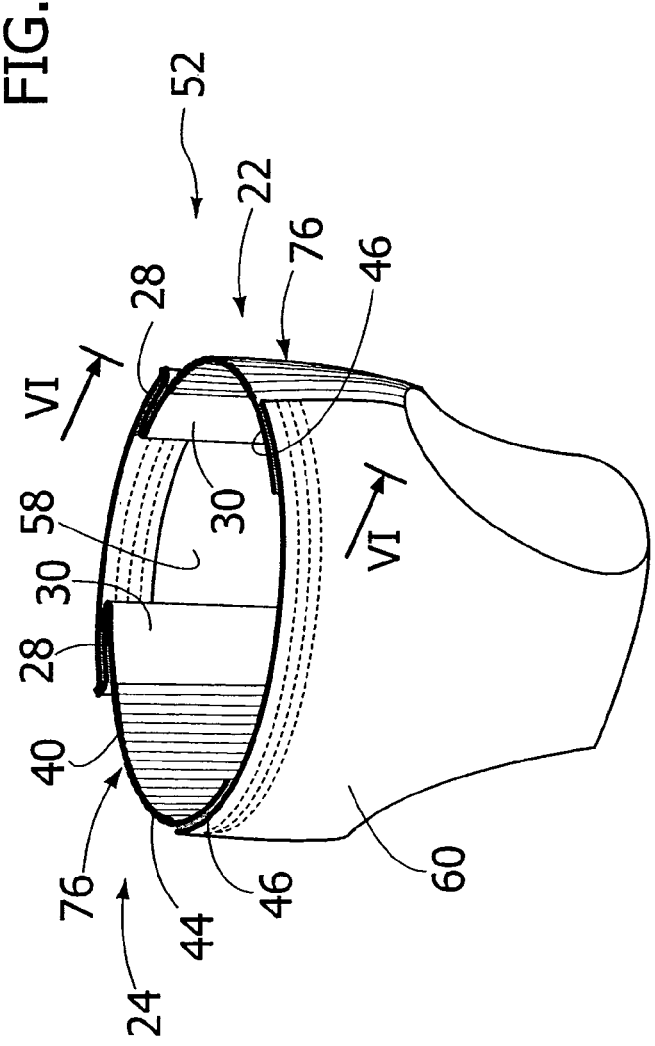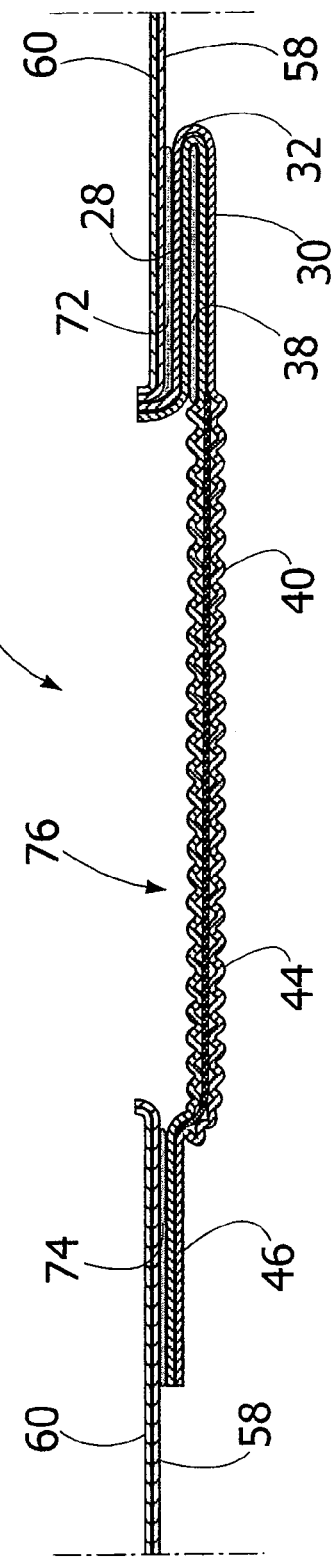

CLOSURE ELEMENT WITH ELASTIC SIDE PANELS FOR ABSORBENT SANITARY PRODUCTS, ABSORBENT SANITARY PRODUCT AND RESPECTIVE MANUFACTURING METHOD

This application is the U.S. national phase of International Application No. PCT/IB2008/000639 filed 7 Mar. 2008 which designated the U.S. and claims priority to European Patent Application No. 07425518.3 filed 8 Aug. 2007, the entire contents of each of which are hereby incorporated by reference.

FIELD OF THE INVENTION

The present invention relates to absorbent sanitary products and it was developed with particular attention to the possible application to pant-like absorbent sanitary products. A typical example of absorbent sanitary products of this kind is represented by the so-called training-pants.

DESCRIPTION OF THE RELATED ART

The document US-A-2002/0111596 (Fletcher et al.), discloses a pant-like absorbent garment having removable side panels that are releasable and refastenable, so that the absorbent garment can be opened and closed on the front side or on the back side of the garment, both on the right side and on the left side. The removable side panels can be reused with a disposable absorbent section of the garment and they are made of partially or completely elasticised material. Each side panel is formed by a strip folded so as to present four parallel branches, with two central branches joined to each other by a fold and with each of the two central branches connected by a respective fold to a respective outer branch. The two outer branches are fastened to respective micro-hook fasteners.

In this known solution, each side panel is an autonomous component. Therefore, automatic machines for the production of garments of this kind must apply two side panels for each garment. On the production line, the side panels must be applied alternatively in mutually opposite directions, which considerably complicates the device that applies the side panels.

The document EP-A-1523968 by the same applicant discloses a closure element formed by two symmetric parts which, after the application to a continuous chain of product blanks, is cut together with the chain of blanks at the plane of symmetry to form two side closures of two adjacent products. This solution enables to apply a single closure element for each product and all closure elements are applied with the same orientation. However, the document EP-A-1523968 does not provide any teachings that allow easily to obtain elastic side panels able to form the flanks of the absorbing product.

OBJECT AND DISCLOSURE OF THE INVENTION

The object of the present invention is to overcome the drawbacks of the prior art.

According to the present invention, said object is achieved by a closure element with elastic side panels having the characteristics set out in claim 1 and by a method for the manufacture of sanitary products having the characteristics set out in claim 13. The claims are an integral part of the technical teachings provided herein in relation to the invention.

As will become readily apparent in the course of the detailed description that follows, the present invention enables to obtain an excellent product with elasticised flanks, with maximum efficiency of the elastic material. The present invention also enables to simplify considerably automatic lines for the manufacture of pant-like sanitary products and with elastic flanks. The present invention provides for applying only one closure element for each product and all the closure elements are applied with the same orientation. With respect to the solution described in the document US-A-2002/0111596, it is not necessary to apply the side panels with alternating orientation. Each closure element originates two side panels as a result of a transverse cut of the continuous chain of product blanks.

According to preferred characteristics of the present invention, it is possible to manufacture pant-like absorbent sanitary products openable in tear-off fashion or openable and re-fastenable.

BRIEF DESCRIPTION OF THE ACCOMPANYING DRAWINGS

Figure 2:
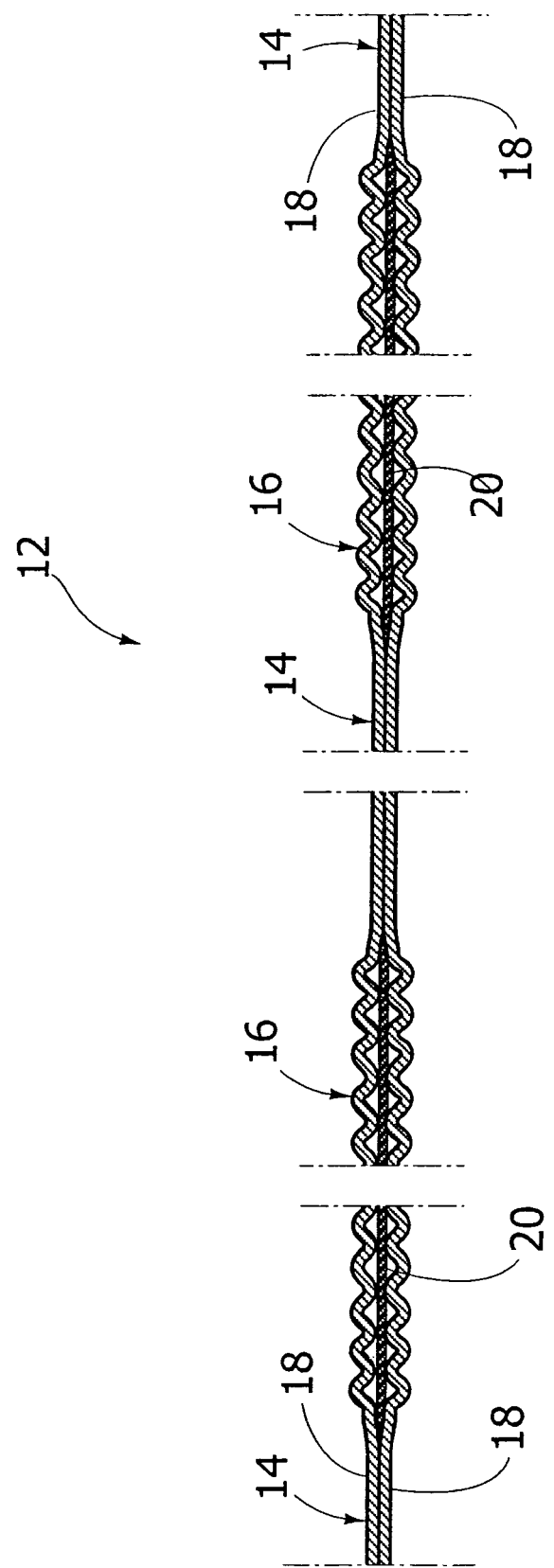
Figure 3:
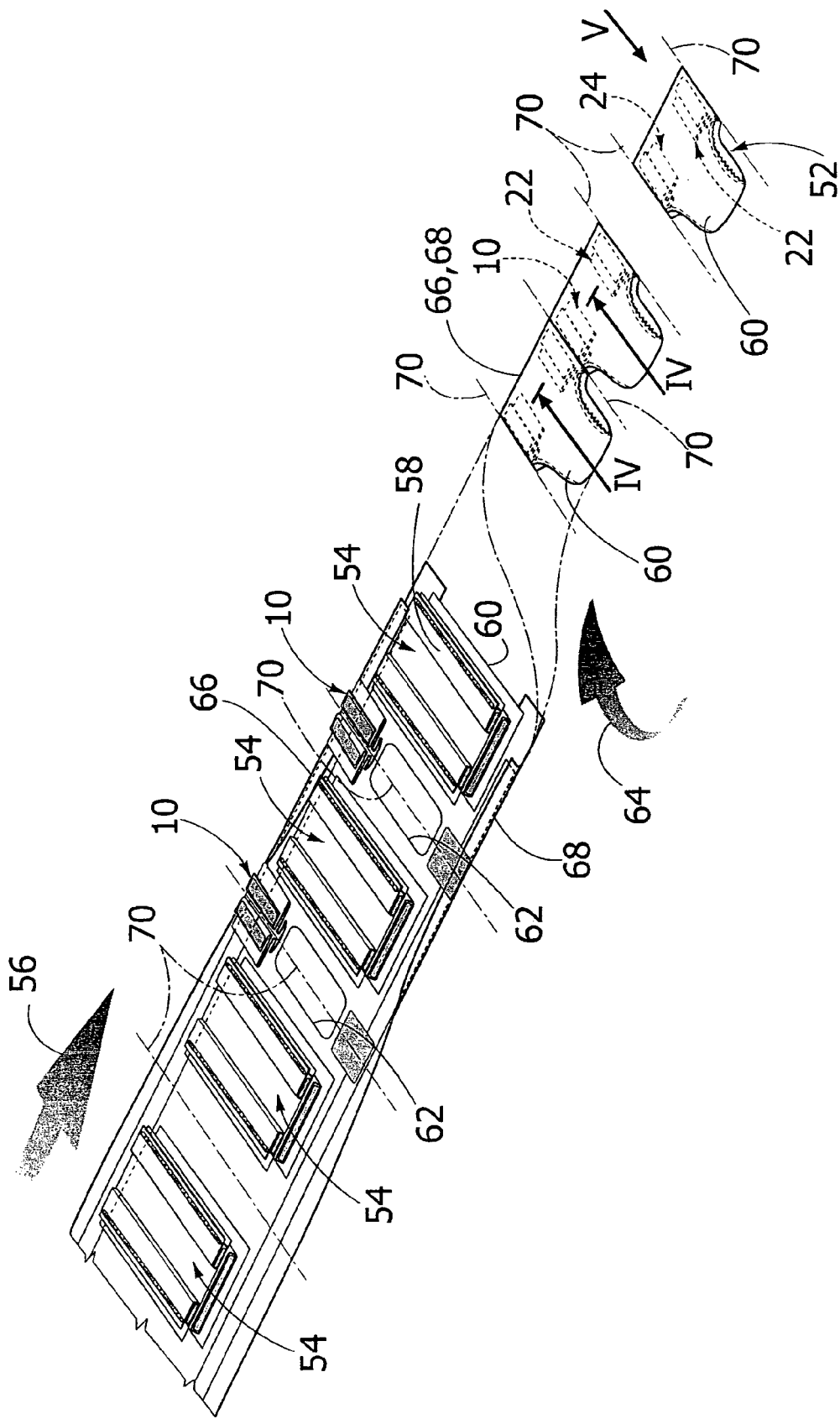
Figure 4:
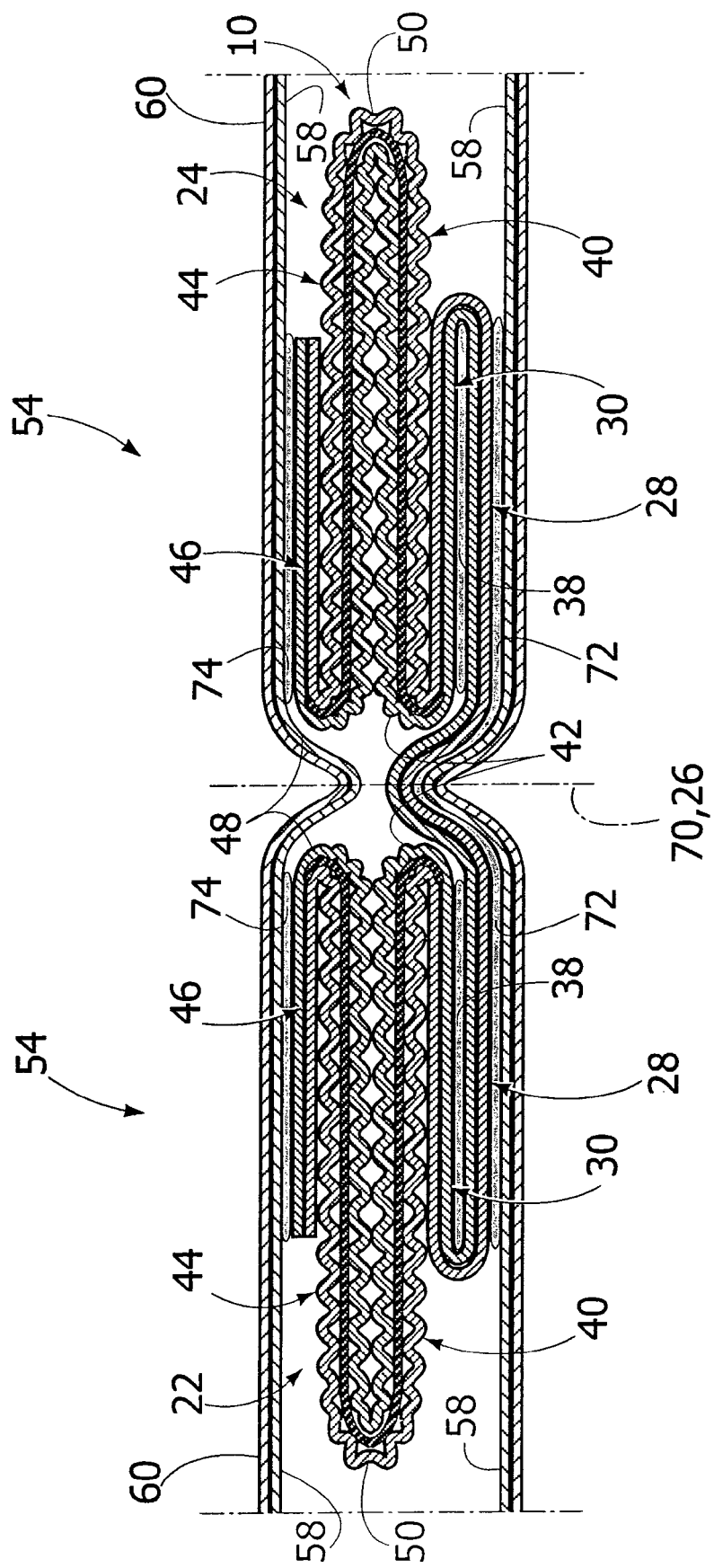
Figure 8:
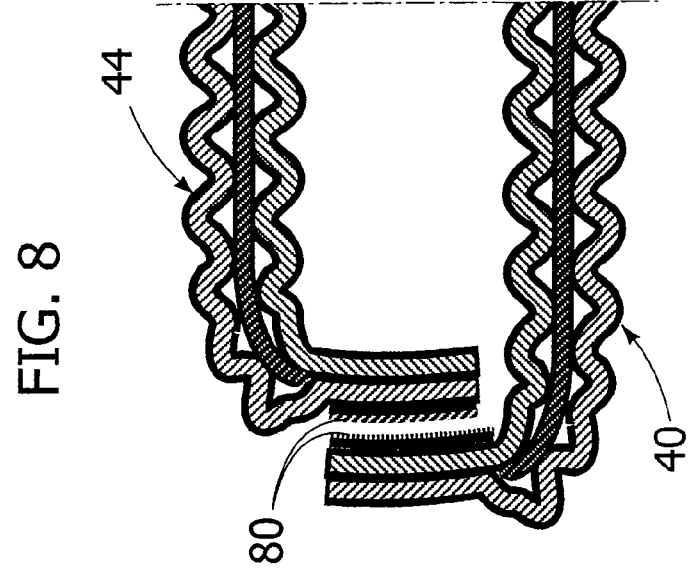
Figure 7:
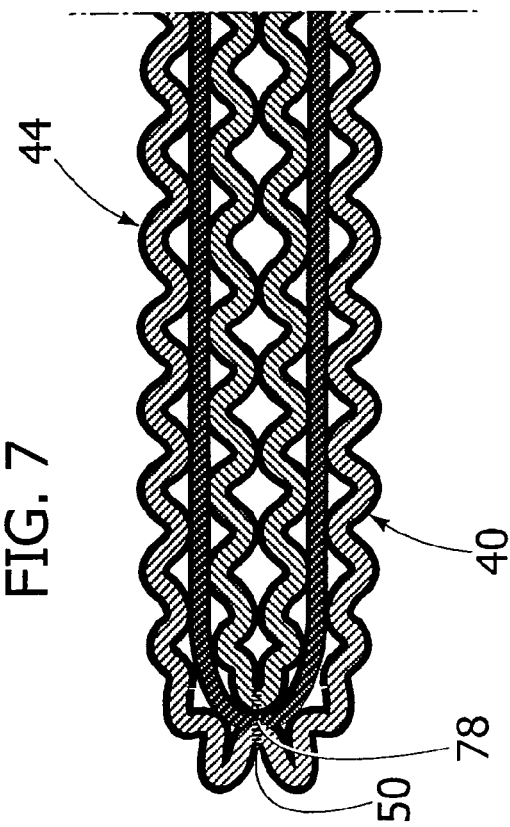
Figure 9:
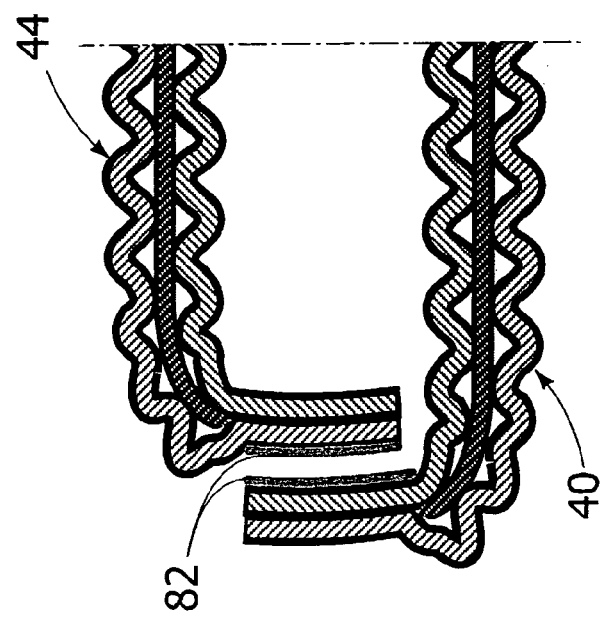
Figure 10:
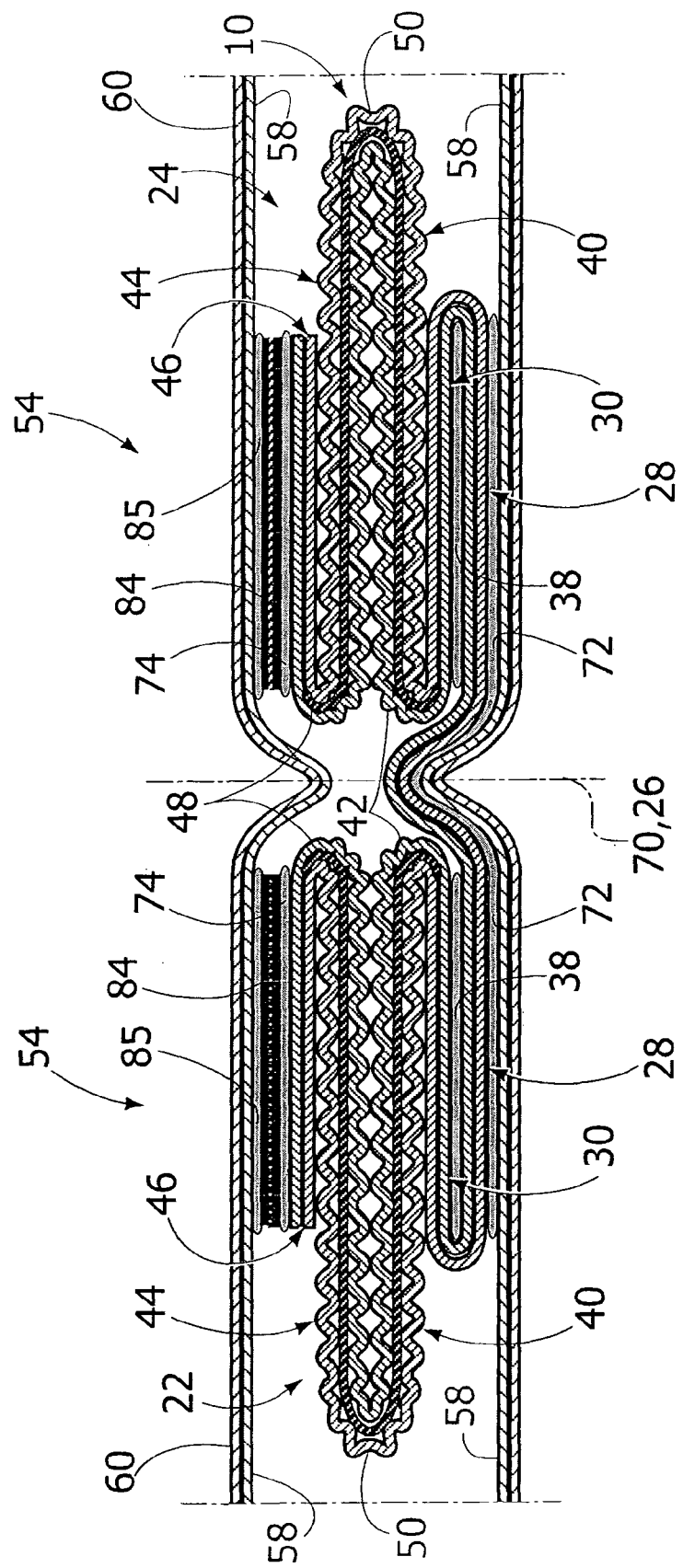

The present invention shall now be described in detail with reference to the accompanying drawings, provided purely by way of non limiting example, in which:

FIG. 1 is a cross section of a closure element with elastic side panels according to the solution described herein, FIG. 2 is a cross section of a strip-shaped element used to manufacture the closure element of FIG. 1, FIG. 3 is a schematic perspective view showing a method for manufacturing absorbent sanitary products, using closure elements according to the solution described herein, FIG. 4 is an enlarged scale section along the line IV-IV of FIG. 3, FIG. 5 is a schematic perspective view showing a sanitary product indicated by the arrow V in figure in conditions of use, FIG. 6 is an enlarged scale section along the line IV-IV of FIG. 5, FIGS. 7, 8 and 9 are enlarged sections showing embodiments of the part indicated by the arrow VII in FIG. 1, and FIG. 10 is a section corresponding to FIG. 4 and showing an additional variant of the solution described herein.

DETAILED DESCRIPTION OF EMBODIMENT EXAMPLES

With reference to FIG. 1, the number 10 indicates a closure element with elastic side panels for pant-like absorbent sanitary products. The element 1 is obtained starting from a strip indicated by 12 in FIG. 2. The strip 12 comprises segments 14 of non elasticised material alternating with segments 16 of elasticised material.

Preferably, the strip 12 comprises two mutually coupled layers of non-woven fabric 18 between which, in the elasticised segments 16, are applied non pre-tensioned elastic films 20, of a commercially available type, which become elastic after mechanical activation of the layers of non-woven fabric 18. Alternatively, the elasticised segments 16 can be obtained by means of pre-tensioned elastic threads 20 (e.g. of the material marketed with the trademark Lycra® by Dupont) or from elastic films 20. The aforesaid elasticisation operations are carried out according to known technologies.

In the absence of a force in the longitudinal direction, in the segments of elasticised material 16 the layers of non-woven fabric 18 can assume an undulated shape as shown in FIG. 2.

Under the action of a longitudinal force, the segments of elasticised material 16 elongate and the layers of non-woven fabric 18 extend.

With reference to FIG. 1, the closure element 10 with elastic side panels according to the solution described herein is obtained by subjecting the strip 12 to a plurality of 180° folds in transverse directions relative to the longitudinal direction of the strip 12. As a result of such folds, the element 10 assumes the conformation shown in FIG. 1.

The closure element 10 comprises two parts 22, 24 that are symmetrical relative to a central transverse plane 26. As shall become clear below, each of the two parts 22, 24 is destined to form a side panel of a sanitary product after a cut of the closure element 10 at the central transverse plane 26.

The closure element 10 comprises a first branch 28 of non elasticised material that extends continuously through the central transverse plane 26. Two second branches 30 of non elasticised material are connected to respective opposite ends of the first branch 28 by means of respective first folds 32, distal relative to the central transverse plane 26. The first branch 28 and the two second branches 30 have respective mutually facing surfaces 34, 36 that are permanently fastened to each other, e.g. by means of respective layers of glue 38 or by welding.

The closure element 10 further comprises two third branches 40 of elasticised material connected to respective ends of the second branches 30 by means of respective second folds 42, proximal relative to the central transverse plane 26. Two fourth branches 44 of elasticised material are connected to respective ends of the two third branches 40 in distal positions relative to the central transverse plane 26. Two fifth branches 46 of non elasticised material are connected to respective ends of the fourth branches 44 by means of respective third folds 48, proximal relative to the central transverse plane 26.

The second folds 42 and the third folds 48 are distanced relative to the central transverse plane 26, so as to leave an empty space around the central plane 26 at a central area of the first branch 38. The third branches 40 and fourth branches 44 extend outwards in the lateral direction beyond the outer lateral ends of the second branches 30 and of the fifth branches 46. Preferably, the second branches 30 and the fifth branches 46 have substantially the same length. In the embodiment shown in FIG. 1, the third branches 40 are connected to the respective fourth branches 44 by means of respective fourth folds 50.

FIG. 3 schematically illustrates a method for the production of pant-like absorbent sanitary products. One of said products is indicated 52 in FIG. 3. The products 52 are obtained starting from a continuous chain of blanks 54 that advances in the longitudinal direction indicated by the arrow 56. The chain of blanks 54 is formed according to known criteria. Typically, the chain of blanks has a sandwich structure comprising a topsheet 58 and a backsheet 60 between which is positioned an absorbent layer. The chain of blanks 54 is provided with openings 62 distanced from each other in the longitudinal direction forming the leg openings of the products 52. FIG. 3 shows a sequence of production of products 52 of the type called cross-direction. In machines of this kind, the continuous longitudinal chain of blanks 54 is subjected to a folding indicated schematically by the arrow 64, as a result of which two opposite longitudinal edges 66, 68 of the chain of blanks 54 are mutually superposed.

Before folding the continuous chain of blanks 54 in the direction indicated by the arrow 64, the closure elements 10 are applied to the chain 54 in positions that are mutually distanced in the longitudinal direction. The closure elements 10 are applied in such a way that the central transverse plane 26 of each element 10 is substantially aligned to a transverse demarcation line 70 between each pair of adjacent blanks 54. The elements of FIG. 10 are applied on the topsheet 58 at one of the two longitudinal edges 66, 68 (at the longitudinal edge 66 in the representation of FIG. 3). A single closure element 10 is applied at each demarcation line 70 and all the closure elements 10 are applied with the same orientation. The closure elements 10 are applied to the chain of blanks 54 by gluing, welding or by micro-hook fasteners. In the example shown in FIG. 3, the first branch 28 of each closure element 10 is glued to the topsheet 58 at the longitudinal edge 66. As a result of the folding in the direction indicated by the arrow 64, the topsheet 58 adjacent to the opposite edge 68 is glued to the fifth branches 46 of each closure element 10.

The closure elements 10 could also be applied in upside down direction relative to the one of FIG. 3, i.e. with the fifth branches 46 glued to the topsheet 58 at the edge 66 and with the opposite edge 68 that is glued to the first branch 28 of each element 10 as a result of the folding of the chain of blanks 54 in the direction indicated by the arrow 64.

After the folding of the chain of blanks 54 according to the arrow 64, the junction area between each pair of adjacent blanks 54 assumes the shape shown in FIG. 4. The demarcation line 70 between two adjacent blanks 54 is positioned substantially at the central transverse plane 26 of each closure element 10. The two parts 22, 24 of each closure element 10 are positioned at opposite sides relative to the demarcation line 70. The first branch 28 of the closure element 10 is fastened to the topsheet 58 of the front or dorsal side of the blank 54 by means of a layer of glue 72 and the fifth branches 46 of the closure element 10 are fastened by means of layers of glue 74 to the topsheet 58 of the opposite side (back or front) of the blanks 54.

In this condition, a transverse cut is executed along the demarcation line 70 between each pair of adjacent blanks 54. With this operation are cut the topsheet 58 and the backsheet 60 of the back side, the first branch 28 of the closure element 10 and the topsheet 58 and the backsheet 60 of the front side. As a result of the cut, the finished products 52 are obtained, one of which is shown in the right part of FIG. 3.

FIG. 5 shows an absorbent sanitary product obtained with the method described above in the condition of use. The product 52 is provided with two side panels 76 of elasticised material, formed by the third branch 40 and by the fourth branch 44 of each part 22, 24 of a closure element 10. As can be noted in particular in FIG. 6, in segments in correspondence with the layers of glue 38, 74 the material is not elasticised. This enables to reduce the thickness of the junction areas and to improve the adhesive connection. The area of elasticised material extends solely at the areas lacking glue and this enables to exploit the elasticised part completely.

In the embodiment described so far, a pant-like product 52 with elasticised flanks is obtained. According to a first variant of the present invention shown in FIG. 7, each closure element 10 can be provided with preferential breaking lines 78 positioned at the fourth folds 50. In this way, each side panel 56 is provided in central position with a tear-off line for the removal of the product 52. Alternatively, the two branches 40, 44 could be mutually connected by means of mechanical welding, heat welding, ultrasound welding, etc.

According to an additional advantageous characteristic of the solution described herein, the product can be openable and refastenable. As shown in FIG. 10, to obtain the capability of opening and refastening the product 52, a micro-hooks fastener 80 can be provided in the connecting area between the third branches 40 and the fourth branches 44 of each closure element 10. The micro-hooks fastener 80 extends at the centre of each side panel 76 and it enables to open, inspect and possibly to refasten the product 52 while it is worn.

As an alternative to the use of a micro-hooks fastener 80, FIG. 9 shows the use of a layer of "pressure sensitive" glue 82 which mutually connects the ends of the third branches 40 and of the fourth branches 44 of each fastening element 10. The layer of glue 82 enables to open and refasten each side panel 76 in a manner similar to a micro-hooks fastener.

As an additional alternative to obtain an openable and refastenable product, the solution shown in FIG. 10 can be used. In this case, the fifth branches 46 of each closure device 10 are connected to the corresponding topsheet 58 by means of micro-hooks 84 fasteners. Each micro-hooks fastener 84 is fastened to the branch 46 and to the topsheet 58 by means of respective layers of glue 74, 85. The closure device 84 can be provided on the front side or on the back side of the product. The micro-hooks fastener 84 also enables to effect an adjustment of the diameter of the waist of the product 52. Alternatively, the micro-hooks fastener 84 can be applied to the first branch 28. As an additional alternative, the first branch 28 and/or the fifth branches 46 can be fastened to the respective topsheets 58 by means of layers of glue of the openable and refastenable type (pressure sensitive).

In the preceding description, the method for the manufacture of products has been described according to a cross-direction configuration, in which the longitudinal extension of the products is transverse relative to the direction of advance of the chain of blanks. The solution described herein can also be applied in "machine-direction" manufacturing methods, in which the product blanks are positioned with their longitudinal extension parallel to the direction of advance of the blanks.

The invention claimed is:

1. A closure element with elastic side panels for disposable pant-like absorbent sanitary products, comprising two parts symmetrical relative to a central transverse plane, each of said parts being intended to form a side panel of an absorbent sanitary product, said closure element comprising:
    a first branch that extends continuously through said central transverse plane, the first branch being made of non-elasticises material consisting of two mutually coupled flat layers of non-woven fabric;
    two second branches connected to respective opposite ends of the first branch by respective first folds, distal relative to said central transverse plane, the first branch and the two second branches having respective mutually facing surfaces permanently fastened to each other, the two second branches being formed of non-elasticised material consisting of two mutually coupled flat layers of non-woven fabric forming continuous extensions of said mutually coupled layers of the first branch;
    two third branches of elasticised material connected to respective ends of the second branches by means of respective second folds proximal and distanced relative to said central transverse plane, the third branches being formed by two undulated layers of non-woven fabric forming continuous extensions of said mutually coupled layers of the second branches and a layer of elastic material set between said undulated layers;
    two fourth branches of elasticised material connected to respective third branches only at respective ends distal relative to said central transverse plane, the fourth branches being formed by two undulated layers of non-woven fabric and a layer of elastic material set between said undulated layers; and
    two fifth branches of non-elasticised material connected to respective ends of the fourth branches by means of respective third folds, proximal and distanced relative to said central transverse plane, the fifth branches consisting of two mutually coupled flat layers of non-woven fabric forming continuous extensions of said undulated layers of non-woven fabric of said fourth branches.

2. Closure element as claimed in claim 1, wherein each third branch is connected to a respective fourth branch by means of a fourth fold.

3. Closure element as claimed in claim 1, wherein each third branch is connected to a respective fourth branch by welding.

4. Closure element as claimed in claim 3, wherein a preferential breaking line is provided at said fourth fold.

5. Closure element as claimed in claim 1, wherein each third branch is connected to the respective fourth branch by means of micro-hooks fasteners.

6. Closure element as claimed in claim 1, wherein each third branch is connected to the respective fourth branch by means of an openable and refastenable layer of glue.

7. Closure element as claimed in claim 1, wherein the fifth branches (46) are fastened to respective micro-hooks fasteners.

8. Closure element as claimed in claim 1, wherein the first branch is fastened to a micro-hooks fastener.

9. A disposable pant-like absorbent sanitary product, comprising an absorbing structure and two elastic side panels, wherein each of said elastic side panels is formed by one half of a closure element according to claim 1.

10. Method for manufacturing disposable pant-like absorbent sanitary products, comprising the steps of:
    forming a continuous longitudinal chain of product blanks having a mutually opposite first and a second longitudinal edge;
    fastening to said chain of blanks closure elements according to claim 1, distanced from each other in longitudinal direction, at a first longitudinal edge, with the central transverse plane of each closure element positioned at a demarcation line between each pair of adjacent blanks;
    folding said chain of blanks so as to mutually superpose said opposite longitudinal edges and fastening the second longitudinal edge to said closure elements; and
    cutting said chain of blanks and said closure elements along said demarcation line so that as a result of the cut the two symmetrical parts of each closure element form respective side panels of two successive products.

11. Method as claimed in claim 10, wherein each closure element is fastened to the first longitudinal edge of the continuous chain of products blanks by means of a system selected among: welding, layer of glue, and micro-hooks fastener.

12. Method as claimed in claim 11, wherein the second longitudinal edge of the continuous chain of products blanks is fastened to each closure element by means of a system selected among: welding, layer of glue, and micro-hooks fastener.

* * * * *